United States Patent [19]

Venäläinen et al.

[11] Patent Number: 4,458,360
[45] Date of Patent: Jul. 3, 1984

[54] PROCEDURE FOR DETERMINING COATING RATES

[75] Inventors: Heikki Venäläinen, Rauha; Rauno Rantanen, Imatra, both of Finland

[73] Assignee: Enso-Gutzeit Oy, Finland

[21] Appl. No.: 382,242

[22] Filed: May 26, 1982

[51] Int. Cl.³ .............................................. G01N 23/22
[52] U.S. Cl. ..................................... 378/50; 378/210
[58] Field of Search ........................................... 378/50

[56] References Cited

U.S. PATENT DOCUMENTS 4,147,931  4/1979  Puumalainen .......................... 378/50
4,377,869  3/1983  Venalainen ............................. 378/50

Primary Examiner—Craig E. Church
Attorney, Agent, or Firm—Toren, McGeady and Stanger

[57] ABSTRACT

The invention concerns a procedure for measuring the coating quantities contained in coating layers deposited on both sides of paper, cardboard or equivalent material in the case in which both coating layers contain the same component emitting characteristic radiation. In the case most commonly encountered, both coating layers consist of the same coating material. In the procedure two functionally mutually independent radiation source/detector pairs are used, between which the coated paper or equivalent is placed. Separately each radiation source/detector pair effects excitation of fluorescent radiation in both coating layers under measurement and the total intensity of the excited radiation present at the detector is measured. If the base weight of the paper or equivalent is known, the coating rates are calculable from the results of measurement obtained. The base weight is most advantageously measured before the coating step with the aid of a separate source of radiation and a transmission detector.

4 Claims, 1 Drawing Figure

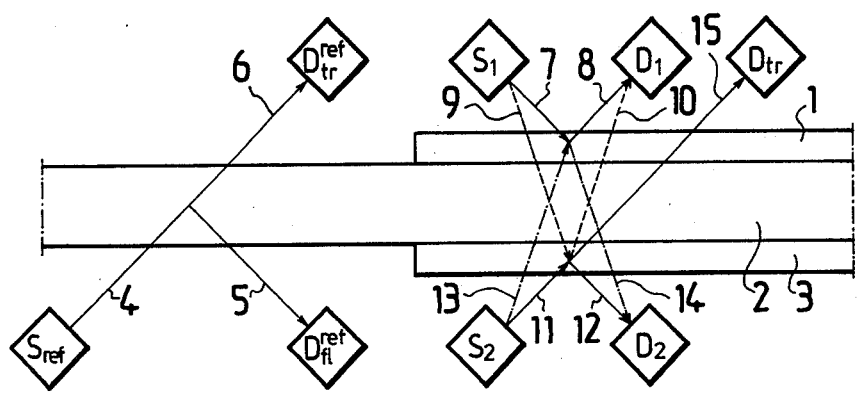

PROCEDURE FOR DETERMINING COATING RATES

The object of the present invention is a procedure for determining coating rates in coating layers deposited on both sides of paper, cardboard or equivalent base material and which contain the same component emitting a characteristic fluorescent radiation, in said procedure the excitation of fluorescent radiation being effected with a primary radiation obtained from a source of radiation and the radiation intensity being measured with a detector.

In prior art there are known methods based on measurement of characteristic fluorescent radiation excited by means of a primary radiation for the measuring of coating rates in one or several superimposed coating layers applied on cardboard or equivalent material. These methods have made use of the absorption in the layer to be measured of the primary radiation and of the fluorescent radiation excited in the layer under the coating layer. When the base material is coated on both sides with coating layers containing the same component emitting characteristic fluorescent radiation, the above-mentioned methods of prior art are no longer usable. A typical example of such cases is a paper web which has been coated on both sides with one and the same coating compound. The object of the present invention is to provide a method for measuring coating rates which is applicable in these cases, and the invention is characterized in that the coated base material is placed between two radiation source/detector pairs functionally independent of each other and that separately for each radiation source/detector pair excitation of fluorescent radiation is effected in the coating layers on both sides of the base material and measurement of the added intensity of the excited radiation, whereby the coating rates are calculable from the results of the measurement obtained and from the base weight of the base material, which is known or is separately determined.

The invention is described in detail in the following with the aid of an example with reference being made to the drawing attached, which presents the measuring of the coating layers on a paper web coated on both sides.

As shown in the drawing, the paper web comprises a topside coating layer 1, a paper course 2 and an underside coating layer 3. The coating layers 1 and 3 consist of a coating compound emitting the same isotope- or X-ray tube-excited characteristic fluorescent radiation and they have been applied on the paper 2 with the same coating unit. For the purpose of measuring the coating rates, a source of radiation $S_{ref}$ emitting a primary radiation 4 has been placed in advance of the coating unit. The fluorescent radiation 5 excited by the primary radiation 4 in the raw paper is measured by means of a detector $D_{fl}^{ref}$ and the primary radiation that has passed through the raw paper, 6, is measured with another detector $D_{tr}^{ref}$. Following after the coating unit, on both sides of the paper web have been disposed radiation source/detector pairs $S_1,D_1$ and $S_2,D_2$, which have been so collimated that the measurements carried out with them do not interfere with each other. The primary radiation 7 emitted by the radiation source $S_1$ excites in the coating layer 1 the fluorescent radiation 8, which is observed by the detector $D_1$. At the same time the primary radiation 9 emitted by the radiation source $S_1$ acts on the coating layer 3, the fluorescent radiation excited herein, 10, also going to the detector $D_1$. Similarly, the primary radiation 11,13 emitted by the radiation source $S_2$ produces in the coating layer 3 the fluorescent radiation 12 and in the coating layer 1 the fluorescent radiation 14, and the fluorescent radiation produced are observed with the detector $D_2$. The primary radiation 15 passing through the coated paper web is furthermore measured with the transmission detector $D_{tr}$.

If we denote $m_1$ = coating rate of the topside coating layer 1
$m_2$ = base weight of the paper course 2
$m_3$ = coating rate of the underside coating layer 3
$I_{fl}^{ref}$ = intensity of the fluorescent radiation measured with detector $D^{ref}$
$I_1$ = intensity of the fluorescent radiation measured with detector $D_1fl$
$I_2$ = intensity of the fluorescent radiation measured with detector $D_2$
$C_1$ = effective activity of the topside measuring pick-up
$C_2$ = effective activity of the underside measuring pick-up
$C_1'$ = ratio $I_1/I_{fl}^{ref}$ measured with a given raw paper containing filler
$C_2'$ = ratio $I_2/I_{fl}^{ref}$ measured with a given raw paper containing filler
$\mu_s$ = "self-absorption coefficient" of the coating
$\mu_c^\sigma$ = combined mass absorption coefficient of the primary and secondary radiations into the coating
$\mu_p^\sigma$ = combined mass absorption coefficient of the primary and secondary radiations into the paper, the intensity of radiation 8 is $C_1 \cdot m_1 \cdot e^{-\mu_s \cdot m_1}$
the intensity of radiation 10 is $C_1 \cdot m_3 \cdot e^{-(\mu_c^\sigma \cdot m_1 + \mu_p^\sigma \cdot m_2)}$
the intensity of radiation 12 is $C_2 \cdot m_3 \cdot e^{\mu_s \cdot m_3}$, and
the intensity of radiation 14 is $C_2 \cdot m_1 \cdot e^{-(\mu_c^\sigma \cdot m_3 + \mu_p^\sigma \cdot m_2)}$.

The coating rates may then be determined by the equations (1) and (2), easily calibrated in practice, $$I_1 \approx C_1[m_1 \cdot e^{-\mu_B \cdot m_1} + m_3 \cdot e^{-(\mu_c^\sigma \cdot m_1 + \mu_p^\sigma \cdot m_2)}] + C_1' \cdot I_{fl}^{ref} \quad (1)$$

$$I_2 \approx C_2[m_3 \cdot e^{-\mu_s \cdot m_3} + m_1 \cdot e^{-(\mu_c^\sigma \cdot m_3 + \mu_p^\sigma \cdot m_2)}] + C_2' \cdot I_{fl}^{ref} \quad (2)$$

When the coating rates are determined in the manner presented, the determination implies information supplied to the computer regarding the base weight ($=m_2$) of the paper that is being coated, and which is obtainable e.g. from a separate, punctiform β base weight measuring instrument monitoring the raw paper. It is however more convenient, and conducive to more accurate results, if the continuous monitoring of the raw cardboard is effected with the aid of a transmission detector mounted on the measuring head measuring the raw cardboard and measuring the primary radiation of $S_{ref}$. It is true that in the latter case no absolutely exact base weights are obtained, but when the calibration of the apparatus as well as subsequent measurements are based on $I_{tr}^{ref}$, changes in the filler content and composition of the raw paper cannot significantly affect the fluorescence yield measured on the opposite side of the paper (changes of the quantity of coating material present as filler cause a variation in the secondary radiation not nearly as strong as in the primary radiation). It is therefore worthwhile to determine $m_2$ for use in equations (1) and (2) from equation (3) and to determine the true weight of the raw paper separately by another method.

$$I_{tr}^{ref} = I_{tr}^{ref}{}_0 \cdot e^{-\mu_p m_2}; \quad m_2 = \frac{\ln(I_{tr}^{ref}{}_0/I_{tr}^{ref})}{\mu_p} \quad (3)$$

$I_{tr}^{ref}$ = transmission intensity measured with $D_{tr}^{ref}$
$F_{tro}^{ref} = I_{tr}^{ref}$ measured with $D_{tr}^{ref}$ with no paper interposed
$\mu_p$ = mass absorption coefficient of the paper for the primary radiation in direction $D_{tr}^{ref}$.

The significance of the raw paper's filler content and composition variations in the result of measurement can also be aliminated by mounting on the measuring head monitoring the coated area, another transmission detector $D_{tr}$ measuring the primary radiation from either $S_1$ or $S_2$ and by determining, to begin with, the total coating rate ($= m_1 + m_3$) with the aid of two transmission detector readings by the equation (4)

$$I_{tr} = C_3 \cdot I_{tr}^{ref} \cdot e^{-\mu_c(m1+m3)}; \quad m_1 + m_3 = \frac{\ln(C_3 \cdot I_{tr}^{ref}/I_{tr})}{\mu_c} \quad (4)$$

$I_{tr}$ = intensity measured with $D_{tr}$
$C_3 = I_{tr}/I_{tr}^{ref}$ when $m_1 = m_3 = 0$.
$\mu_c$ = mass absorption coefficient of the coating for the primary radiation in direction $D_{tr}$
and the ratio $m_1/m_3$ thereafter directly from the simplified equations for $I_1$ and $I_2$: $I_1 = C_1 \cdot m_1 + C_1' \cdot I_{fl}^{ref}$ and $I_2 = C_2 \cdot m_3 + C_2' \cdot I_{fl}^{ref}$, whereby $m_1$ and $m_3$ are calculable by equations (5) and (6)

$$m_1 = \frac{C_2(I_1 - C_1' \cdot I_{fl}^{ref})}{C_1(I_2 - C_2' \cdot I_{fl}^{ref})} \cdot m_3 \quad (5)$$

$$m_3 = \frac{\ln(C_3 \cdot I_{tr}^{ref}/I_{tr})}{\mu_c} - \frac{C_2(I_1 - C_1' \cdot I_{fl}^{ref})}{C_1(I_2 - C_2' \cdot I_{fl}^{ref})} \cdot m_3 \quad (6)$$

If the filler distribution of the paper in the z direction is considerably variable, it may in some instances be indicated, when accurate results are desired, to mount on the reference measuring head a source/detector pair also on the other side of the paper.

Since the influence of variations in moisture content and base weight on the accuracy of measurement is exceedingly small when for exciting sources of radiation for instance γ isotopes are used, the errors caused by the punctiformity of the reference source are usually negligible. However, when coating heavy raw papers or cardboards, it is worthwhile to omit the determination of total coating rate based on transmission and to perform the measurements exclusively based on fluorescences, owing to the fact that the fluorescence yield factor of the coating on the opposite side of the raw paper in equations (1) and (2) diminishes very strongly with increasing base weight of the raw paper, and owing to the fact that the error of measurement incurred through moisture content variations has effect almost exclusively on this factor.

It is obvious to a person skilled in the art that different embodiments of the invention are not confined to the example presented and may instead vary within the scope of the claims following below.

We claim:

1. Procedure for determining coating rates in applying layers (1,3) to the opposite sides of a paper material web (2), such as paper, cardboard and the like, each of the coating layers containing the same component which emits characteristic fluorescent radiation, including the steps of directing primary radiation from one of a radiating isotope and an X-ray tube against the coated web, exciting fluorescent radiation in the coating layers based on the directed primary radiation, and measuring the intensity of the fluorescent radiation emitted as a result of the directed primary radiation, wherein the improvement comprises arranging two mutually functionally dependent primary radiation source/fluorescent radiation detector pairs ($S_1,D_1$ and $S_2,D_2$) each on an opposite side of the coated paper material web (2), and separately directing primary radiation from each of said radiation sources ($S_1,S_2$) into the coated paper material web so that each source excites fluorescent radiation in both of the coating layers, and measuring the added intensity of the fluorescent radiation from both coating layers with each corresponding detector ($D_1,D_2$) of the radiation source/detector pairs so that the coating rates are calculable from the measurement of the fluorescent radiation obtained and from the base weight of the paper material web.

2. Procedure according to claim 1, including the steps of measuring the coating rates in conjunction with the coating of the paper material web, measuring the base weight of the paper material web prior to applying the coating layers (1,3) by directing a source of radiation ($S_{ref}$) located on one side of the paper material web (2) and with a transmission detector ($D_{tr}^{ref}$) located on the opposite side of the paper material web from the source of radiation ($S_{ref}$).

3. Procedure according to claim 1 or 2, including the step of measuring the primary radiation (15) passing through the coated paper material web (2) with a transmission detector ($D_{tr}$) disposed in conjunction with one of the radiation source/detector pairs ($S_1,D_1$ and $S_2,D_2$) so that from the result of the measurement the added coating rate of the coating layers (1,3) can be calculated.

4. Procedure according to claim 1 or 2, including the step of collimating the radiation source/detector pairs ($S_1,D_1$ and $S_2,D_2$) for carrying out the measurements so that the radiation source/detector pairs do not interfere with one another.

* * * * *